US012684224B2

(12) United States Patent
Meyerson et al.

(10) Patent No.: US 12,684,224 B2
(45) Date of Patent: Jul. 14, 2026

(54) TELEHEALTH COMMUNICATIONS

(71) Applicant: Welch Allyn, Inc., Skaneateles Falls, NY (US)

(72) Inventors: Craig M. Meyerson, Syracuse, NY (US); Daniel Shirley, Raleigh, NC (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 259 days.

(21) Appl. No.: 18/173,393

(22) Filed: Feb. 23, 2023

(65) Prior Publication Data

US 2023/0300448 A1     Sep. 21, 2023

Related U.S. Application Data

(60) Provisional application No. 63/269,427, filed on Mar. 16, 2022.

(51) Int. Cl.
| | |
|---|---|
| *H04N 23/62* | (2023.01) |
| *G16H 40/67* | (2018.01) |
| *G16H 80/00* | (2018.01) |
| *H04N 23/611* | (2023.01) |
| *H04N 23/695* | (2023.01) |

(52) U.S. Cl.
CPC ............. *H04N 23/62* (2023.01); *G16H 40/67* (2018.01); *G16H 80/00* (2018.01); *H04N 23/611* (2023.01); *H04N 23/695* (2023.01)

(58) Field of Classification Search
None
See application file for complete search history.

(56) References Cited

U.S. PATENT DOCUMENTS

| | | | |
|---|---|---|---|
| 8,169,463 | B2 | 5/2012 | Enstad et al. |
| 8,248,448 | B2 | 8/2012 | Feng et al. |
| 8,274,544 | B2 | 9/2012 | Kurtz et al. |
| 8,994,881 | B2 | 3/2015 | Shyu |
| 9,032,461 | B2 | 5/2015 | Tucker et al. |
| 9,265,429 | B2 | 2/2016 | St. Pierre et al. |
| 9,361,021 | B2 | 6/2016 | Jordan et al. |
| 9,615,055 | B2 | 4/2017 | Book |
| 9,762,953 | B2 | 9/2017 | Lee |
| 10,165,159 | B2 | 12/2018 | Cassini et al. |
| 10,455,182 | B2 | 10/2019 | Lee et al. |
| 10,702,174 | B2 | 7/2020 | Fasciano |
| 10,972,655 | B1 * | 4/2021 | Ostap .................... H04N 7/147 |

(Continued)

FOREIGN PATENT DOCUMENTS

| | | |
|---|---|---|
| WO | 2011/116340 A2 | 9/2011 |
| WO | 2021/185244 A1 | 9/2021 |
| WO | 2021/189400 A1 | 9/2021 |

*Primary Examiner* — Duc Nguyen
*Assistant Examiner* — Assad Mohammed
(74) *Attorney, Agent, or Firm* — Merchant & Gould P.C.

(57) ABSTRACT

A system for providing telehealth consultations. The system includes a display device located in a patient environment, and a camera operatively connected to the display device. The camera is configured to capture a video stream of the patient environment. The system includes a telehealth device remotely located with respect to the patient environment. The telehealth device initiates a telehealth consultation on the display device. The telehealth device causes the camera to adjust the video stream of the patient environment during the telehealth consultation.

15 Claims, 12 Drawing Sheets

(56) References Cited

U.S. PATENT DOCUMENTS

| 10,976,908 | B2 | 4/2021 | Freeman et al. |
| 11,360,634 | B1 * | 6/2022 | Chang ................... G06F 3/0481 |
| 11,589,006 | B1 * | 2/2023 | Acevedo ............... G06V 10/25 |
| 11,862,302 | B2 * | 1/2024 | Pinter .................... G06N 3/045 |
| 2007/0299316 | A1 | 12/2007 | Haslehurst et al. |
| 2010/0194845 | A1 | 8/2010 | Cho et al. |
| 2011/0285825 | A1 * | 11/2011 | Tian .......................... G06T 5/90 |
| | | | 348/47 |
| 2014/0275928 | A1 * | 9/2014 | Acquista ............. A61N 1/3987 |
| | | | 600/382 |
| 2016/0182814 | A1 | 6/2016 | Schwesinger et al. |
| 2016/0188829 | A1 * | 6/2016 | Southerland ............ H04N 7/15 |
| | | | 705/2 |
| 2017/0032092 | A1 * | 2/2017 | Mink ................. G06Q 30/0241 |
| 2017/0235905 | A1 | 8/2017 | Santiago, Jr. |
| 2018/0107341 | A1 * | 4/2018 | Aurongzeb ............. G06F 3/017 |
| 2018/0226158 | A1 | 8/2018 | Fish et al. |
| 2019/0298184 | A1 * | 10/2019 | Jain ...................... A61B 5/6876 |
| 2020/0058410 | A1 * | 2/2020 | Khouri, III ............ G16H 80/00 |
| 2020/0121199 | A1 | 4/2020 | Freeman et al. |
| 2020/0335190 | A1 | 10/2020 | Chung et al. |
| 2020/0357493 | A1 | 11/2020 | Kelly et al. |
| 2021/0038088 | A1 | 2/2021 | Atallah et al. |
| 2021/0250540 | A1 | 8/2021 | Gao et al. |
| 2021/0314659 | A1 | 10/2021 | Gao et al. |
| 2021/0369115 | A1 * | 12/2021 | Zatvan ................. A61B 5/1032 |
| 2022/0215970 | A1 * | 7/2022 | Trpkovski .......... G07C 9/00904 |
| 2022/0230741 | A1 * | 7/2022 | Wynnik ................ G16H 10/60 |

* cited by examiner

800

Receive Instruction to Follow Object          802

Identify Object          804

Generate Command(s) to Track Movements of Object          806

Send Command(s)          808

900

902
Initiate Telehealth
Consultation

904
Adjust Playback of Currently
Playing Media Content

906
Allocate Portion of Display
for Telehealth Consultation

908
Adjust Camera Field of View
Based on Commands

1000

1002
Receive Consultation Request

1004
Acquire Relevant Patient Data

1006
Initiate Consultation

1008
Display Relevant Patient Data with Video Stream of Patient

1010
Receive Trigger Event

1012
Adjust Display of Relevant Patient Data

TELEHEALTH COMMUNICATIONS

BACKGROUND

Telehealth is becoming more popular as a way to provide healthcare. While telehealth consultations provide efficiencies for healthcare workers, there are often delays and costs associated with setting up equipment for telehealth consultations. Also, it is desirable to leverage consumer devices to monitor and interact with patients as acute healthcare shifts to the home.

SUMMARY

In general terms, the present disclosure relates to telehealth communications. In one possible configuration, a system consolidates devices inside a patient environment for conducting telehealth consultations. In another possible configuration, a telehealth device provides a smart data display during telehealth consultations. Various aspects are described in this disclosure, which include, but are not limited to, the following aspects.

One aspect relates to a system for providing telehealth consultations. The system comprises: a display device located in a patient environment; a camera operatively connected to the display device, the camera configured to capture a video stream of the patient environment; and a telehealth device remotely located with respect to the patient environment, the telehealth device including: at least one processing device; and a memory device storing instructions which, when executed by the at least one processing device, cause the telehealth device to: initiate a telehealth consultation on the display device; and cause the camera to adjust the video stream of the patient environment during the telehealth consultation.

Another aspect relates to a device for conducting a telehealth consultation. The device comprises: at least one processing device; and a memory device storing instructions which, when executed by the at least one processing device, cause the device to: receive a request for the telehealth consultation; determine relevant patient data based on a type of health condition or a symptom included in the request for the telehealth consultation; acquire the relevant patient data from at least one of a monitoring device located in a patient environment and an electronic medical record system; and display the relevant patient data and a video stream of the patient environment during the telehealth consultation.

Another aspect relates to a method of conducting a telehealth consultation. The method comprises: receiving a request for the telehealth consultation; determining relevant patient data based on a type of health condition or a symptom included in the request for the telehealth consultation; acquiring the relevant patient data from at least one of a monitoring device located in a patient environment and an electronic medical record system; and displaying the relevant patient data together with a video stream of the patient environment during the telehealth consultation.

DESCRIPTION OF THE FIGURES

The following drawing figures, which form a part of this application, are illustrative of the described technology and are not meant to limit the scope of the disclosure in any manner.

DETAILED DESCRIPTION

Figure 1:
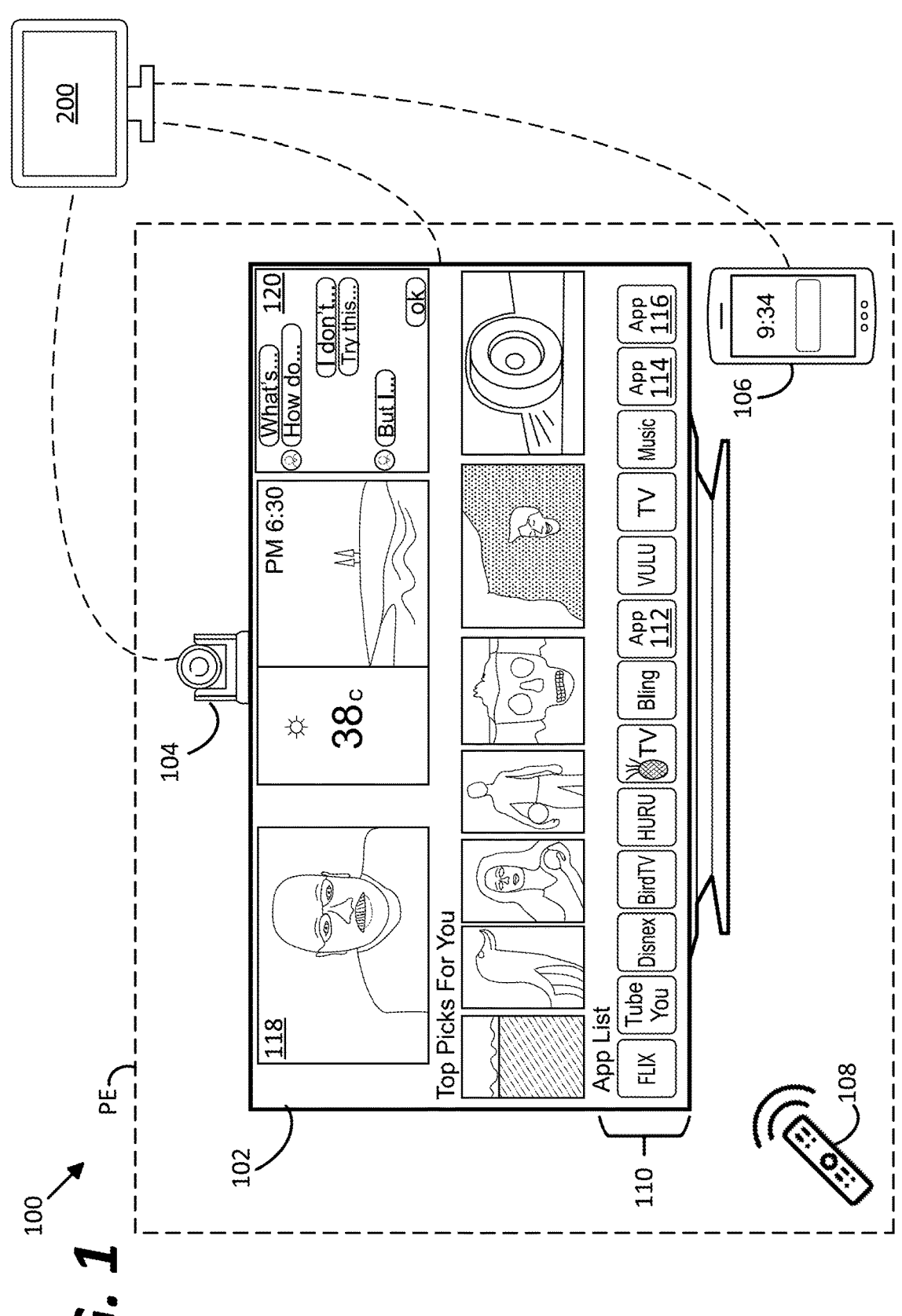
FIG. 1 illustrates an example of a healthcare communications system that includes a telehealth device in communication with devices remotely located in a patient environment including a smart TV, a camera, and a mobile device.

FIG. 1 illustrates an example of a healthcare communications system 100 that includes a telehealth device 200 in communication with devices located in a patient environment PE. As described herein, telehealth is the distribution of health-related services and information via electronic information and telecommunication technologies including any communication technique, including wired, wireless, Internet, radio frequency (RF), and the like.

In the example shown in FIG. 1, the telehealth device 200 is remotely located with respect to the patient environment PE. In one example, the patient environment PE is a patient room within a healthcare facility such as a hospital, a nursing home, a long-term care facility, and the like. In another example, the patient environment PE is a patient's home.

As shown in the example provided in FIG. 1, the patient environment PE includes a smart TV 102, a camera 104, and a mobile device 106. In this example, the patient environment PE further includes a remote control 108 that can be used by a patient to control operation of the smart TV 102 and other devices present in the patient environment PE. The smart TV 102 is an example of a display device, and the concepts described herein are similarly applicable to additional types of display devices such as monitors, video displays, and the like.

The smart TV 102 is a television with integrated Internet and interactive features that allows the patient, in addition to viewing traditional broadcast or cable/satellite media, to view streaming media content including videos, music, and photos, and browse the Internet. Also, the smart TV 102 when used along with the camera 104 enables the patient to engage in a telehealth consultation having two-way video communications. The smart TV 102 is an example of a computing device. The smart TV 102 will be described in more detail with reference to FIG. 3.

In some examples, the camera 104 is integrated with the smart TV 102 such that the smart TV 102 and the camera 104 comprise a single electronic device. In alternative examples, the camera 104 is a separate device that mounts onto the smart TV 102 or is otherwise positionable separately from the smart TV 102. In some examples, the camera 104 is a pan-tilt-zoom (PTZ) camera that allows a clinician to control the movement and position of the camera 104 from a remote location such as by using controls on the telehealth device 200. The camera 104 will be described in more detail with reference to FIG. 4.

The mobile device 106 is an example of a portable computing device. Examples of the mobile device 106 include a smartphone, a tablet computer, and the like. The mobile device 106 can be operated by the patient while viewing media content on the smart TV. In some examples, the mobile device 106 can be used by the patient to control operation of the smart TV 102 and other devices present in the patient environment PE.

In the example shown in FIG. 1, the smart TV 102 displays a home screen having an application list 110 that includes a plurality of applications that can be selected by the patient such as by using the remote control 108. The application list 110 can include various streaming service apps for viewing media content such as television series, movies, music, and the like.

The application list 110 can include an app 112 for viewing various educational videos that explain the patient's diagnosis, prognosis, and/or treatment. In some examples, the app 112 includes videos that instruct the patient to perform exercises as part of their treatment such as to move their limbs in accordance with a mobility plan. In further examples, the app 112 include games that the patient can play to keep entertained, while also learning about their diagnosis, prognosis, and treatment, and/or performing exercises as part of their treatment.

The application list 110 further includes an app 114 that can be selected by the patient using the remote control 108 to request or initiate a telehealth consultation with a remote clinician. The telehealth consultation uses the camera 104 to stream a video of the patient to the telehealth device 200 operated by the remote clinician, while the smart TV 102 displays a video stream of the remote clinician in a portion 118 of the display on the smart TV 102. In this manner, the healthcare communications system 100 utilizes the smart TV 102 and the camera 104 to provide two-way video communications between the patient and the remote clinician.

When the patient is viewing content from another app that has been selected from the application list 110 (e.g., a movie selected from a streaming service app, or a game selected from the app 112), a portion of the screen displaying the content on the smart TV 102 can be used to display the telehealth consultation with the remote clinician. Thus, the app 114 enables two-way video communications for telehealth consultations while the smart TV 102 is being used for playback of content from any of the plurality of applications in the application list 110.

The application list 110 further includes an app 116 that can be selected by the patient using the remote control 108 to display a chat with the remote clinician or one or more additional caregivers. As shown in FIG. 1, the chat is displayed in a portion 120 of the display on the smart TV 102. Thus, the app 116 enables text message communications while the smart TV is being used to display content from any of the plurality of applications in the application list 110.

In some examples, the patient can use the remote control 108 to select letters and numbers from a keyboard displayed on the smart TV 102 to write and second a message to the chat. In other examples, the patient can use the mobile device 106 to write and send a message to the chat, which then appears in the portion 120 of the display when received in the chat. In further examples, the smart TV 102 or the mobile device 106 can recognize speech from the patient, and can convert the speech into text to draft a message for receipt in the chat.

As shown in FIG. 1, a telehealth device 200 is in communication with the smart TV 102, the camera 104, and the mobile device 106. As described above, the telehealth device 200 is remotely located with respect to the patient environment PE. In examples where the patient environment is a patient room in a healthcare facility, the telehealth device 200 can be located in a different location within the healthcare facility such as in a nurses' station or in a control room, or can be located offsite such as in a separate building or campus. In examples where the patient environment is the patient's home, the telehealth device 200 can be located in a healthcare facility such that the telehealth device 200 is used to provide hospital-at-home services.

Figure 2:
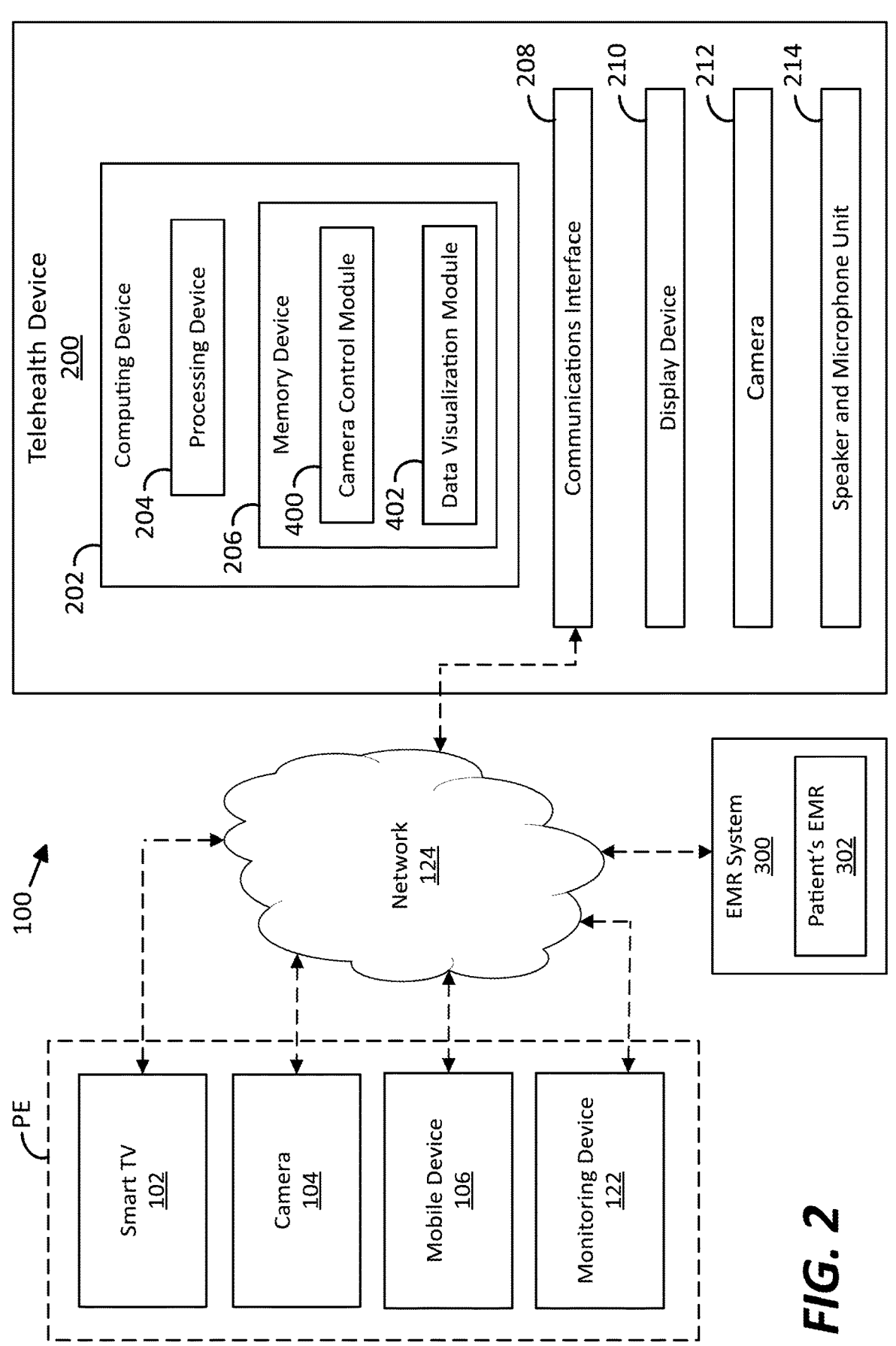
FIG. 2 schematically illustrates the healthcare communications system of FIG. 1.

FIG. 2 schematically illustrates an example of the healthcare communications system 100. In the example shown in FIG. 2, the telehealth device 200 is in communication with various devices located in the patient environment PE via a communications network 124. For example, the telehealth device 200 is in communication via the communications network 124 with the smart TV 102, the camera 104, and the mobile device 106, which are shown in FIG. 1. In this example, the telehealth device 200 is in further communication with a monitoring device 122 that is located inside the patient environment PE via the communications network 124.

The monitoring device 122 includes one or more sensors for measuring and recording physiological parameters of the patient in the patient environment PE. For example, the monitoring device 122 can include sensors for measuring and recording blood oxygen saturation (SpO2), non-invasive blood pressure (both systolic and diastolic), respiration rate, pulse rate, temperature, electrocardiogram (ECG), heart rate variability, and the like.

In some examples, the monitoring device 122 is a spot monitor, similar to the one described in U.S. Pat. No. 9,265,429, which is herein incorporated by reference in its entirety. In further examples, the monitoring device 122 is a pad that is placed under a mattress upon which the patient is resting for measuring and recording physiological parameters of the patient. In further examples, the monitoring device 122 includes a wearable device such as a fitness tracker or smart watch for measuring and recording physiological parameters of the patient.

The communications network 124 can include any type of wired or wireless connections or any combinations thereof. The communications network 124 includes the Internet. In some examples, the communications network 124 includes wireless connections such as cellular network connections including 4G or 5G. Wireless connections can also be accomplished using Wi-Fi, ultra-wideband (UWB), Bluetooth, and the like.

The telehealth device 200 is also in communication with an electronic medical record (EMR) system 300 via the communications network 124. The telehealth device 200 can acquire health information from an electronic medical record (EMR) 302 (alternatively termed electronic health record (EHR)) of the patient that is stored in the EMR system 300. The EMR of the patient can include health information such as lab results, scans, administered medications, health interventions including surgeries and procedures performed on the patient, records of the physiological parameters acquired from the monitoring device 122, and other information.

The telehealth device 200 includes a computing device 202 having a processing device 204 and a memory device 206. The processing device 204 is an example of a processing unit such as a central processing unit (CPU). The processing device 204 can include one or more CPUs. In some examples, the processing device 204 can include one or more microcontrollers, digital signal processors, field-programmable gate arrays, or other electronic circuits.

The memory device 206 operates to store data and instructions for execution by the processing device 204. The memory device 206 includes computer-readable media, which may include any media that can be accessed by the telehealth device 200. The computer-readable media can include computer readable storage media and computer readable communication media. In the example shown in FIG. 2, the memory device 206 stores a camera control module 400 and a data visualization module 402, which are described in more detail below.

Computer readable storage media includes volatile and nonvolatile, removable, and non-removable media implemented in any device configured to store information such as computer readable instructions, data structures, program modules, or other data. Computer readable storage media can include, but is not limited to, random access memory, read only memory, electrically erasable programmable read only memory, flash memory, and other memory technology, including any medium that can be used to store information that can be accessed by the telehealth device 200. The computer readable storage media is non-transitory.

Computer readable communication media embodies computer readable instructions, data structures, program modules or other data in a modulated data signal such as a carrier wave or other transport mechanism and includes any information delivery media. The term "modulated data signal" refers to a signal that has one or more of its characteristics set or changed in such a manner as to encode information in the signal. By way of example, computer readable communication media includes wired media such as a wired network or direct-wired connection, and wireless media such as acoustic, radio frequency, infrared, and other wireless media. Combinations of any of the above are within the scope of computer readable media.

The telehealth device 200 includes a communications interface 208 that operates to connect the telehealth device 200 to the communications network 124 for communication with the devices in the patient environment PE such as the smart TV 102, the camera 104, the mobile device 106, and the monitoring device 122, and for communication with the EMR system 300. The communications interface 208 can include both wired interfaces and wireless interfaces.

The telehealth device 200 further includes a display device 210 for displaying a video stream of the patient captured by the camera 104, and a camera 212 for providing a video stream of the remote clinician for display on the smart TV 102 in the patient environment PE.

The telehealth device 200 further includes a speaker and microphone unit 214 for outputting audio of the patient captured in the patient environment PE, and for capturing audio of the remote clinician for playback in the patient environment PE. Accordingly, the display device 210, the camera 212, and the speaker and microphone unit 214 can be used to provide two-way video communications between the telehealth device 200 and the smart TV 102.

Figure 3:
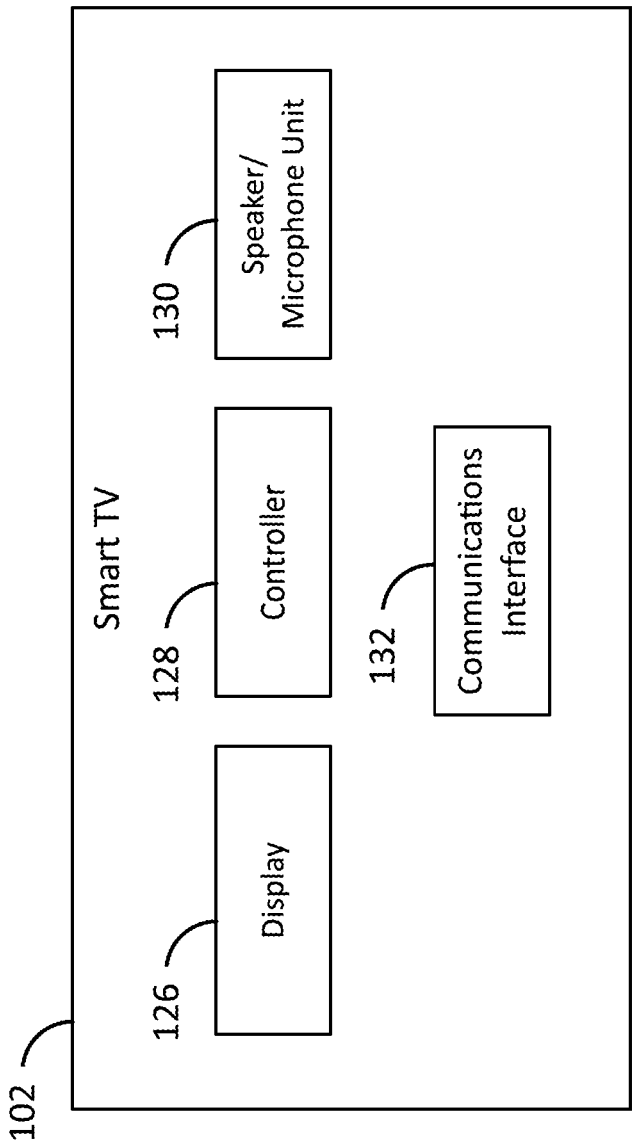
FIG. 3 schematically illustrates additional example details of the smart TV of FIG. 1.

FIG. 3 schematically illustrates additional example details of the smart TV 102. In the example shown in FIG. 3, the smart TV 102 includes a display 126, a controller 128, a speaker and microphone unit 130, and a communications interface 132.

The display 126 operates to display content on the smart TV 102 such as media content from the applications in the application list 110, and traditional television broadcasting. The display 126 can also operate to display a video stream of the remote clinician captured by the camera 212 of the telehealth device 200. The display 126 can display the video stream of the remote clinician while simultaneously displaying content such as an episode of a television series, a movie, music, an educational (e.g., eLearning) video, photos, a game, and the like.

The speaker and microphone unit 130 operates to output audio from the media content such as an episode of a television series, a movie, an educational video, a game, and the like. The speaker and microphone unit 130 also operates to output audio from the video stream of the remote clinician captured by the speaker and microphone unit 214 of the telehealth device 200. Also, the speaker and microphone unit 130 operates to record audio of the patient. Accordingly, the display 126 and the speaker and microphone unit 130 are able to provide two-way video communications between the smart TV 102 and the telehealth device 200.

The controller 128 is an example of a computing device that can control operation of the smart TV 102. The controller 128 can share similarities with the computing device 202 of the telehealth device 200 such that it can include similar processing and memory devices.

The communications interface 132 operates to connect the smart TV 102 to the communications network 124 for communication with the telehealth device 200. The communications interface 132 can include both wired interfaces and wireless interfaces.

Figure 4:
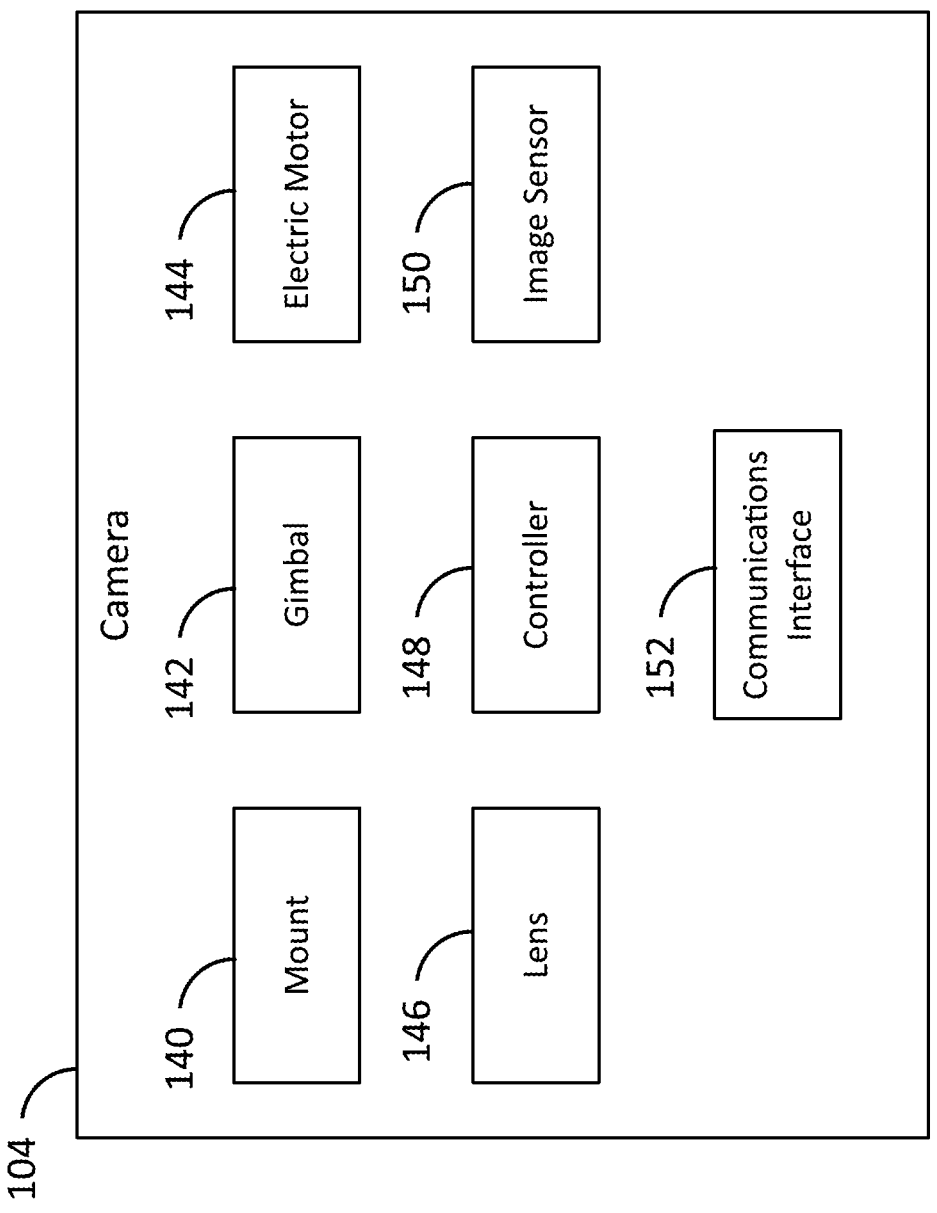
FIG. 4 schematically illustrates additional example details of the camera of FIG. 1.

FIG. 4 schematically illustrates additional example details of the camera 104. In the example shown in FIG. 4, the camera 104 includes a mount 140, a gimbal 142, an electric motor 144, a lens 146, a controller 148, an image sensor 150, and a communications interface 152.

The mount 140 operates to fix the camera 104 relative to the smart TV 102. In one example, the mount 140 includes a mechanical interface such as a clamp to physically attach the camera 104 to the smart TV 102. In other examples, the mount 140 includes a mechanical interface that can physically attach the camera 104 to a surface adjacent to the smart TV 102 such as a furniture item on which the smart TV 102 is supported, or to a portion of a wall proximate to where the smart TV 102 is supported. Additional examples are contemplated.

As described above, the camera 104 in certain examples is a pan-tilt-zoom (PTZ) camera. The gimbal 142 allows for movement of the image sensor 150. For example, the gimbal 142 can be used to pan the image sensor 150 left to right, and to tilt the image sensor 150 up and down to adjust the field of view of the video stream captured by the image sensor 150.

The electric motor 144 is connected to the gimbal 142. As will be described in more detail below, the electric motor 144 can be used to move the gimbal 142 to pan left to right, and to tilt up and down based commands received from the controller 148.

In some examples, the electric motor 144 is connected to the lens 146 to control an optical zoom of the camera 104. For example, the lens 146 is mounted in front of the image sensor 150, and the electric motor 144 can move the lens 146 relative to the image sensor 150 to adjust the focal length of the lens 146 to zoom-in and zoom-out based the commands received from the controller 148. Alternatively, the controller 148 can perform digital zoom on the video stream captured by the image sensor 150 such as by enlarging pixels within an area of interest.

The controller 148 is an example of a computing device that can control operation of the camera 104. For example, the controller 148 can instruct the electric motor 144 to move the gimbal 142 such as to pan the image sensor 150 left and right, and to tilt the image sensor 150 up and down. Additionally, the controller 148 can instruct the electric motor 144 to move the lens 146 relative to the image sensor 150 to adjust optical zoom. In further examples, the controller 148 can provide digital zoom on the video stream captured by the image sensor 150.

The communications interface 152 allows the camera 104 to connect to the smart TV 102 and/or to the communications network 124. The communications interface 152 can include both wired interfaces (e.g., USB port) and wireless interfaces (e.g., Bluetooth connection).

Figure 5:
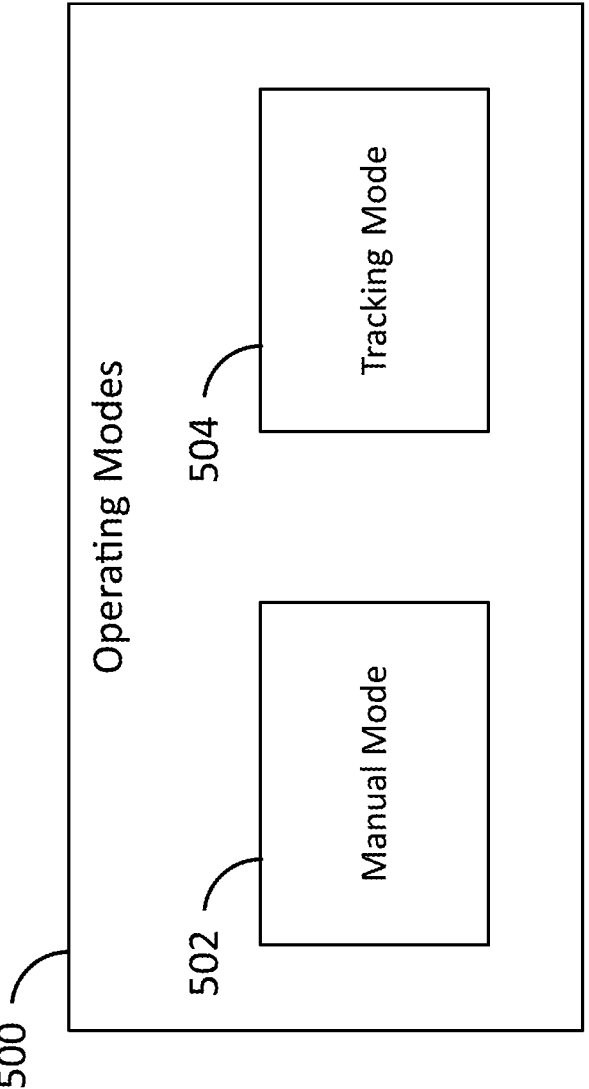
FIG. 5 schematically illustrates examples of operating modes under which the camera of FIG. 4 can be configured to operate.

FIG. 5 schematically illustrates examples of operating modes 500 under which the camera 104 can be configured to operate. In certain examples, the camera 104 receives instructions from the camera control module 400 installed on the telehealth device 200 to move the gimbal 142 using the electric motor 144 to adjust the field of view of the camera 104.

In the example shown in FIG. 5, the camera 104 can operate under a manual mode 502 in which the remote clinician uses one or more controls provided by the telehealth device 200 to manually control the field of view of the camera 104. Alternatively, the camera 104 can operate under a tracking mode 504 in which the camera 104 automatically adjusts the field of view to track an object of interest identified by the remote clinician on the telehealth device 200.

Figure 6:
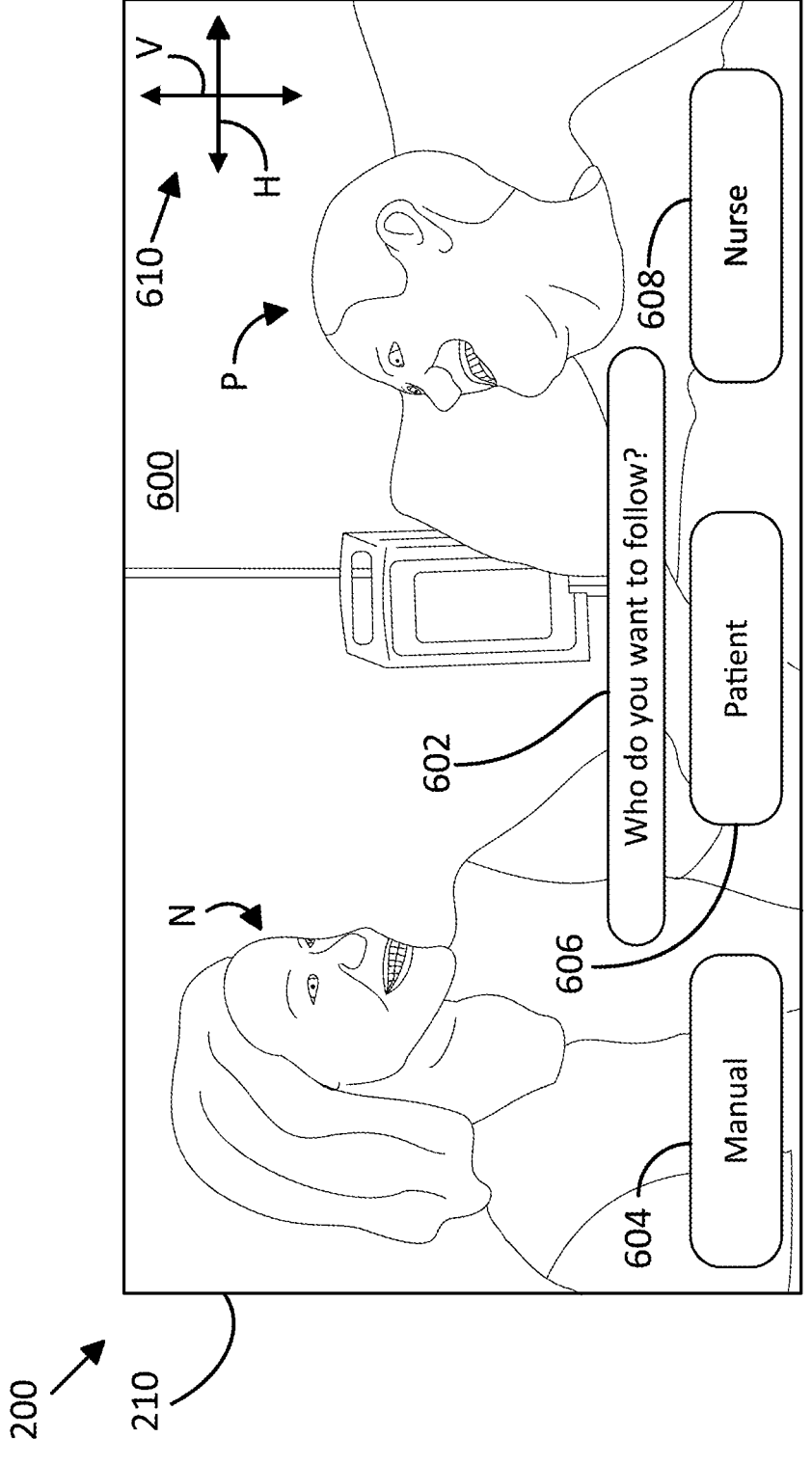
FIG. 6 illustrates an example of a user interface displayed on a display device of the telehealth device of FIG. 1.

FIG. 6 illustrates an example of a user interface 600 displayed on the display device 210 of the telehealth device 200. As shown in FIG. 6, the user interface 600 displays a video stream of a patient P and a nurse N captured by the camera 104 inside the patient environment PE. The user interface 600 further displays a message 602 such as "Who do you want to follow?" and displays one or more options for the remote clinician to select. In the example shown in FIG. 6, the remote clinician can select an icon 604 to perform the manual mode 502.

Figure 7:
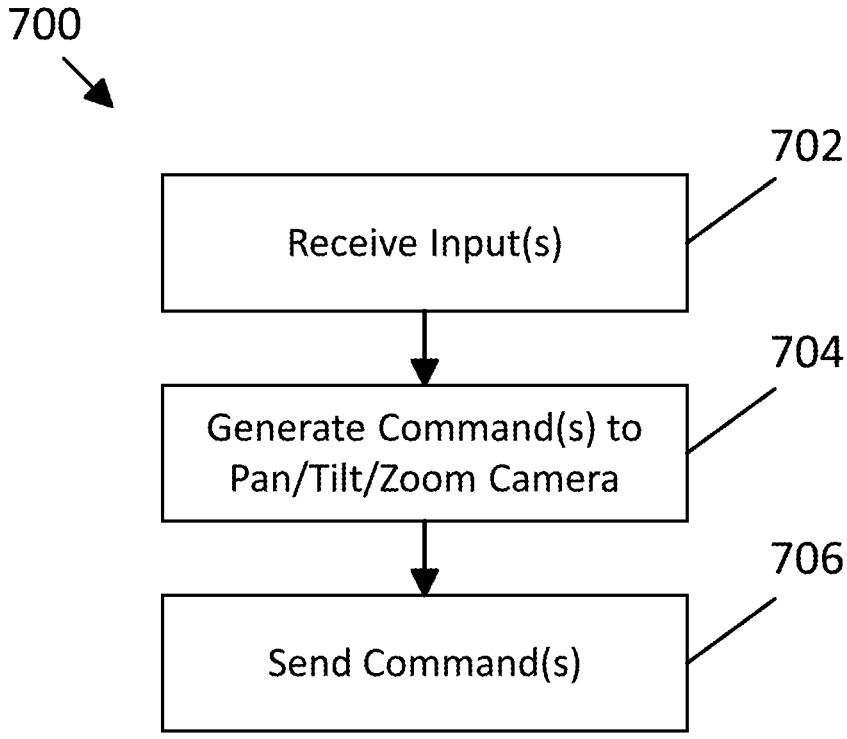
FIG. 7 schematically illustrates an example of a method of conducting a telehealth consultation on the telehealth device of FIG. 1 under a manual mode.

FIG. 7 schematically illustrates an example of a method 700 of conducting a telehealth consultation on the telehealth device 200 under the manual mode 502. The method 700 can be performed by the camera control module 400 installed on the telehealth device 200. The method 700 can be performed in response to the remote clinician selecting the icon 604 displayed on the user interface 600 shown in FIG. 6.

As shown in FIG. 7, the method 700 includes an operation 702 of receiving one or more inputs from the remote clinician. The one or more inputs can be received in a plurality of different ways at least some of which are described herein.

As an illustrative example, the remote clinician can enter inputs by using a tool 610 displayed on the user interface 600. In this example, the remote clinician can select a left or right side of a horizontal axis H using a mouse cursor to enter an input to pan the gimbal 142 of the camera 104 left or right, and can select an upper or lower portion of a vertical axis V using the mouse cursor to enter an input to tilt the gimbal 142 of the camera 104 up or down.

As a further illustrative example, the remote clinician can click on the video stream displayed in the user interface 600, and while holding the click, can move the mouse to enter inputs to pan and/or tilt the gimbal 142. As a further illustrative example, the remote clinician can select one or more keyboard arrow keys to enter inputs to pan and/or tilt the gimbal 142. In yet further examples, the display device 210 of the telehealth device 200 includes a touchscreen allowing the remote clinician to use their fingers or a stylus to enter inputs to pan and/or tilt the gimbal 142. In yet further examples, the camera 212 of the telehealth device 200 can recognize gestures from the remote clinician to enter inputs to pan and/or tilt the gimbal 142. Additional examples for the remote clinician to enter inputs to pan and/or tilt the gimbal 142 are possible.

The remote clinician can also scroll a wheel in clockwise or counterclockwise directions on the mouse to enter inputs to zoom in or out. In another example, the remote clinician while clicking on the video stream displayed in the user interface 600, can move the mouse up or down to enter inputs to zoom in or out. As a further illustrative example, the remote clinician can use one or more keys on a keyboard to enter inputs to zoom in or out. In examples where the display device 210 includes a touchscreen, the remote clinician can move their fingers together or apart on the touchscreen to enter inputs to zoom in or out. In further examples, the camera 212 can recognize gestures from the remote clinician to enter inputs to zoom in or out. Additional examples for the remote clinician to enter inputs to zoom in or out are possible.

Next, the method 700 further includes an operation 704 of converting the one or more inputs into commands for panning, tilting, and/or zooming the camera 104 in the patient environment PE. For example, operation 704 can include generating commands for the controller 148 to instruct the electric motor 144 to move the gimbal 142 of the camera 104 to pan the image sensor 150 left or right, and to tilt the image sensor 150 up or down. Additionally, operation 704 can include generating commands for the controller 148 to instruct the electric motor 144 to move the lens 146 relative to the image sensor 150 to zoom in or out. In further examples, operation 704 can include generating commands to provide a digital zoom on the video stream displayed in the user interface 600 such as by enlarging pixels within an area of interest.

Next, the method 700 includes an operation 706 of sending the commands to the camera 104 located in the patient environment PE. In some examples, the camera 104 receives the commands directly from the telehealth device 200 via the connection through the communications network 124. In alternative examples, the smart TV 102 receives the commands from the telehealth device 200 via the communications network 124, and the camera 104 thereafter receives the commands from a connection to the smart TV 102.

Referring back to FIG. 6, the remote clinician can also identify one or more objects of interest in the video stream displayed in the user interface 600 to perform the tracking mode 504 on the camera 104 located in the patient environment PE. For example, the remote clinician can select an icon 606 to automatically track the field of view of the camera 104 the movement of the patient P. Alternatively, the remote clinician can select an icon 608 to automatically track the field of view of the camera 104 with the movement of the nurse N who is present inside the patient environment PE. In further examples, the remote clinician can select an icon to automatically track an object such as a medical device including, for example, a spot monitor, hospital bed, and the like. An illustrative example of performing the tracking mode 504 based on the selection of the icons 606, 608 will next be described with reference to FIG. 8.

Figure 8:
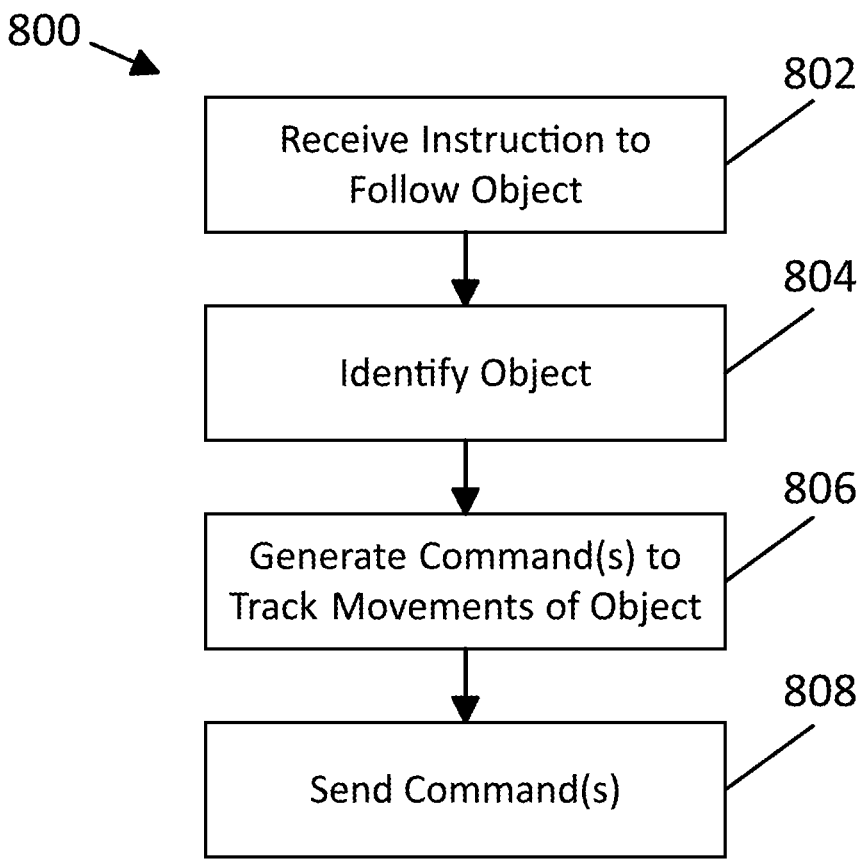
FIG. 8 schematically illustrates an example of a method of conducting a telehealth consultation on the telehealth device of FIG. 1 under a tracking mode.

FIG. 8 schematically illustrates an example of a method 800 of conducting a telehealth consultation on the telehealth device 200 under the tracking mode 504. The method 800 can be performed by the camera control module 400 installed on the telehealth device 200.

The method 800 includes an operation 802 of receiving an instruction to follow an object in the video stream captured by the camera 104 in the patient environment PE. For example, operation 802 can include receiving a selection of the icon 606 displayed on the user interface 600 to follow the patient P. As a further example, operation 802 can include receiving a selection of the icon 608 displayed on the user interface 600 to follow the nurse N.

Additional icons can be displayed in the user interface 600 to track additional persons including doctors, medical specialists, and family members, and to track additional types of objects such as medical devices including a spot monitor, a hospital bed, and the like.

In some examples, operation 802 can include using the speaker and microphone unit 214 to receive a verbal input from the remote clinician that can be processed by the computing device 202 of the telehealth device 200 for recognizing an object such as person or piece of medical equipment. Further examples of receiving the instructions in operation 802 are possible.

Next, the method 800 includes an operation 804 of identifying the object in the video stream captured by the camera 104 in the patient environment PE. As an illustrative example, a person such as the patient P or the nurse N can be identified by facial recognition. For example, an image of the patient P's face is captured and stored in the EMR 302 when the patient P is admitted to the healthcare facility, and the telehealth device 200 can retrieve the image from the EMR 302 via the communications network 124. Thereafter, the telehealth device 200 uses the image to identify the patient P in the video stream captured by the camera 104.

As another example, the telehealth device 200 can recognize a signal from a tag worn by the patient P to identify the patient in the video stream captured by the camera 104. The signal can be sensed by a sensor on the smart TV 102 or the camera 104, and the signal can be communicated to the telehealth device 200 via the communications network 124. In examples where the object is a medical device, the telehealth device 200 can identify the object by recognizing its shape (e.g., the shape of a hospital bed or the shape of a spot monitor), or by recognizing a signal from a tag attached to the medical device. Additional examples of identifying the object in operation 804 are possible.

Next, the method 800 includes an operation 806 of generating commands for the camera 104 to track the movement of the object identified in operation 804, followed by an operation 808 of sending the commands to the camera 104 via the communications network 124. The commands are received by the camera 104 either directly from the telehealth device 200 via the communications network 124, or alternatively, the camera 104 receives the commands from the smart TV 102, which receives the commands via the communications network 124.

In some examples, the commands are generated and sent by the telehealth device 200 each time the telehealth device 200 detects movement of the object. In alternative examples, operation 806 can include generating a command for the camera 104 to track the movement of the object identified in operation 804, and thereafter the camera 104 tracks the movement of the object such that telehealth device 200 does not generate commands each time the object moves. Instead, the camera 104 recognizes the movements of the object, and the controller 148 of the camera 104 instructs the electric motor 144 to move the gimbal 142 to pan left and right and/or to tilt up and down based on the movements of the object detected by the camera 104. Also, the controller 148 can instruct the electric motor 144 to move the lens 146 to zoom in when the object moves away from the camera, or to zoom out when the object moves toward the camera.

In some examples, the camera 104 can use facial recognition to identify a person and track their movements. In further examples, the camera 104 can use motion sensing to follow a moving object such as a patient or a caregiver in the patient environment PE.

Figure 9:
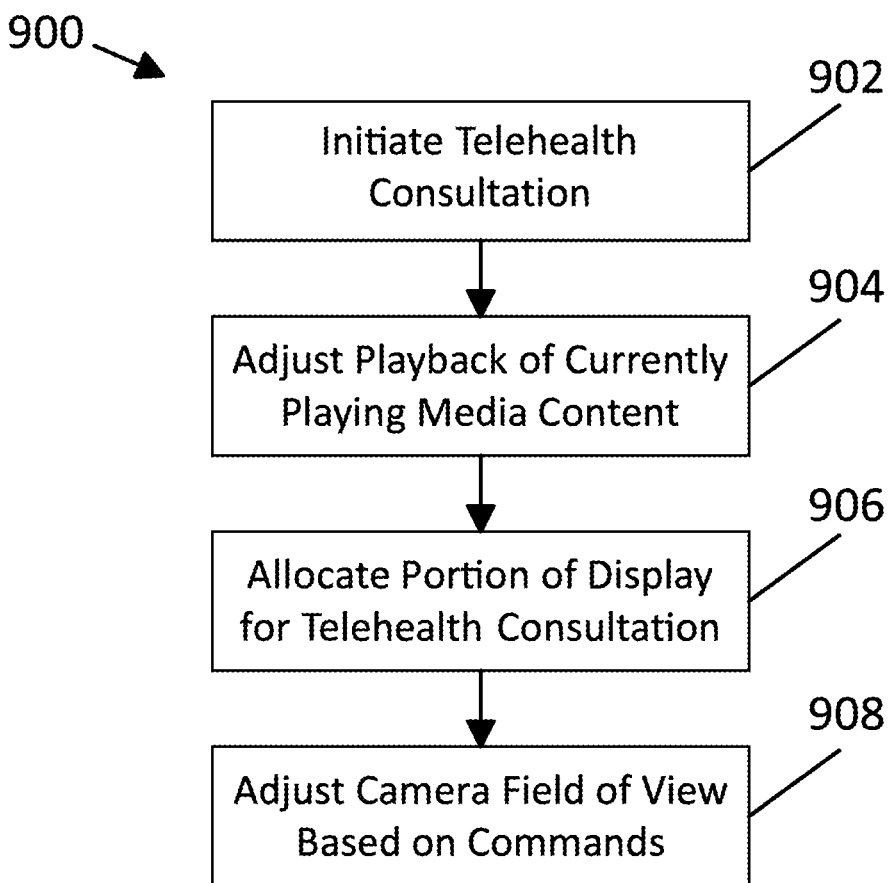
FIG. 9 schematically illustrates an example of a method of conducting a telehealth consultation by the telehealth device of FIG. 1.

FIG. 9 schematically illustrates an example of a method 900 of conducting a telehealth consultation using the telehealth device 200. Advantages of the method 900 can include reducing barriers to connecting with patients via video communications by reducing the steps, time, and costs often associated with telehealth consultations.

As shown in FIG. 9, the method 900 includes an operation 902 of initiating the telehealth consultation. As an example, the telehealth consultation can be initiated following acceptance of a telehealth consultation request on the telehealth device 200 by the remote clinician. The telehealth consultation request can be generated by the patient P using the smart TV 102 or the mobile device 106, and can be routed to the telehealth device 200 for acceptance by the remote clinician via the communications network 124. In certain examples, the app 114 displayed on the smart TV 102 (see FIG. 1) can be selected by the patient using the remote control 108 to request or initiate the telehealth consultation with the remote clinician.

Operation 902 can include security measures to ensure compliance with the Health Insurance Portability and Accountability Act of 1996 (HIPAA), which is a federal law that requires the creation of national standards to protect sensitive patient health information from being disclosed without the patient's consent or knowledge. For example, telehealth consultation request can be generated after the camera 104 captures an image of the patient and facial recognition is performed on the captured image by the controller 128 of the smart TV 102 or the computing device 202 of the telehealth device 200 to confirm the identity of the patient. When the identity of the patient is not confirmed, the telehealth consultation request is not generated, or the telehealth consultation is otherwise not initiated such that the method 900 terminates. In further examples, the identity of the patient can be confirmed by other means such as by using at least one of an admissions, transfer, discharge (ATD) data feed, and bed or patient location determination by a real-time locating system (RTLS), and any combination thereof. In further examples, the telehealth consultation request and any information or data exchanged during the telehealth consultation can be encrypted to provide further data security.

When the smart TV 102 is being used by the patient P for consuming media content, the method 900 can include an operation 904 of adjusting playback of the media content on the smart TV 102 to prevent the patient P from being distracted. For example, operation 904 can include pausing the playback of the media content during the telehealth consultation. In some examples, the playback of the media content is adjusted by lowering or muting the volume of the media content, and/or by decreasing or minimizing the display of the media content without pausing the media content to reduce distraction during the telehealth consultation. In further examples, operation 904 can prevent the patient P from adjusting the playback of the media content (e.g., prevent the patient from increasing the volume) and/or from selecting new media content for playback on the smart TV 102 during the telehealth consultation. Additional examples of adjusting the playback of the media content on the smart TV 102 are possible.

Next, the method 900 includes an operation 906 of allocating a portion of the display 126 of the smart TV 102 for displaying a video stream of the remote clinician captured by the camera 212 and speaker and microphone unit 214 of the telehealth device 200. As an example, operation 906 can include allocating the portion 118 shown in FIG. 1 for displaying the video stream of the remote clinician on the smart TV 102 during the telehealth consultation. In some examples, operation 906 displays the video stream of the remote clinician while also displaying media content from one or more applications included in the application list 110. In some further examples, operation 906 displays the video stream of the remote clinician while also displaying the messaging chat with the remote clinician (see portion 120 in FIG. 1).

Next, the method 900 includes an operation of adjusting a field of view of the camera 104 based on commands received during the telehealth consultation. In some examples, the field of view of the camera 104 is manually adjusted, in accordance with the method 700. In alternative examples, the field of view of the camera 104 is automatically adjusted to track the movement of an object such as the patient, in accordance with the method 800.

In some further examples, the method 900 can include sharing views of one or more applications being displayed on the smart TV 102 and the telehealth device 200. For example, when the patient is viewing an educational video from the app 112 on the smart TV 102, a view of the educational video can also be displayed on the telehealth device 200. In such examples, the remote clinician can view what the patient is watching on the smart TV 102. This allows the remote clinician to provide feedback such as when the patient has a question based on the educational video that is being output on the smart TV 102 in the patient environment PE.

Figure 10:
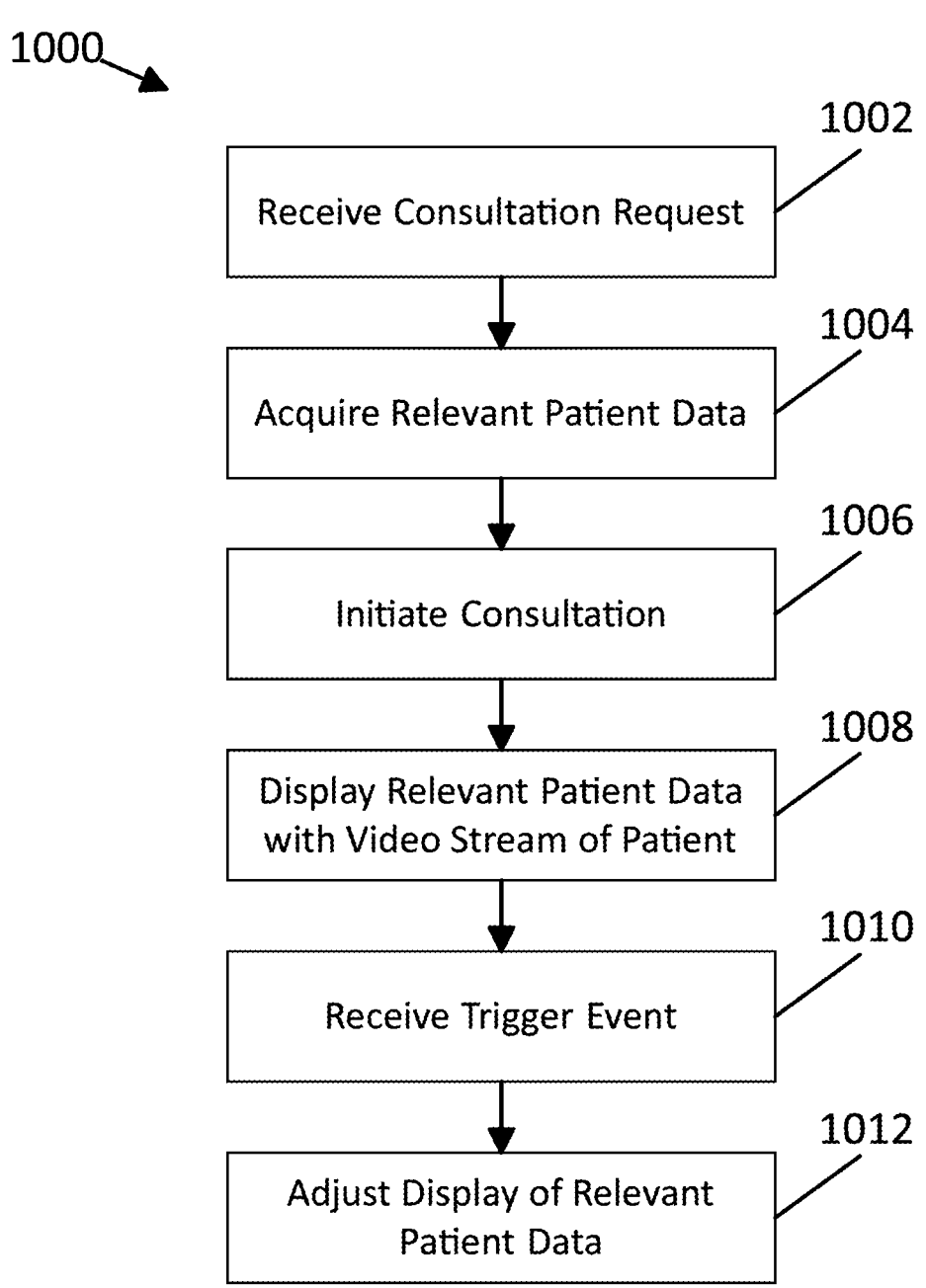
FIG. 10 schematically illustrates another example of a method of conducting a telehealth consultation by the telehealth device of FIG. 1.

FIG. 10 schematically illustrates another example of a method 1000 of conducting a telehealth consultation. The method 1000 when performed by the telehealth device 200 provides an automatic smart data display for viewing by the remote clinician during the telehealth consultation with the patient. For example, the method 1000 enables the telehealth device 200 to acquire relevant patient data and display the data during the telehealth consultation allowing for faster clinical analysis. This can reduce the time to provide a medical intervention, which can improve clinical outcomes for critical health conditions such as stroke, sepsis, and hypoxia.

The method 1000 includes an operation 1002 of receiving a telehealth consultation request. In accordance with the examples described above, the telehealth consultation request can be generated by the patient using the smart TV 102 or the mobile device 106, and can be routed to the telehealth device 200 via the communications network 124. In certain examples, the app 114 displayed on the smart TV 102 (see FIG. 1) can be selected by the patient using the remote control 108 to generate and send the telehealth consultation request. In further examples, the telehealth consultation request can be generated by a caregiver who is located in the patient environment PE such as the nurse N or a family member of the patient P (e.g., see FIG. 6).

Figure 11:
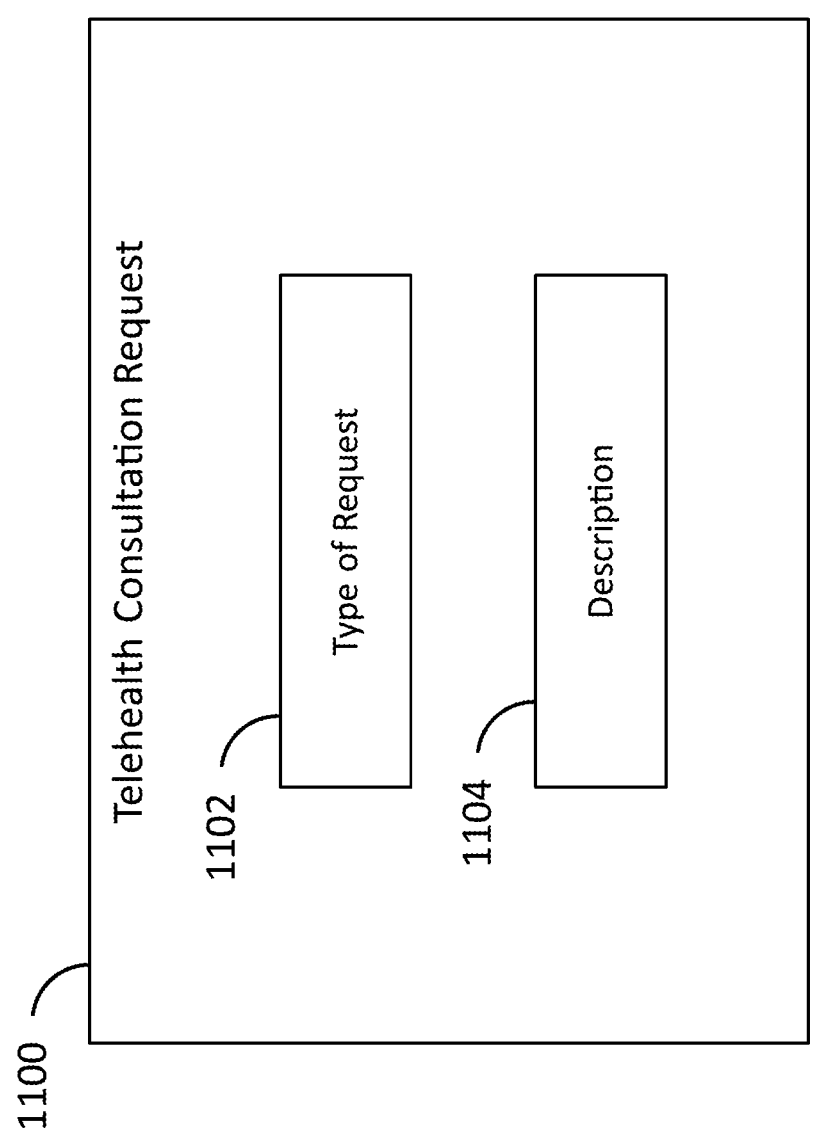
FIG. 11 schematically illustrates an example of a telehealth consultation request generated by the healthcare communications system of FIG. 1.

FIG. 11 schematically illustrates an example of a telehealth consultation request 1100. The telehealth consultation request 1100 includes a request type 1102, and in some instances, can also include a description 1104 that briefly describes patient symptoms and/or a reason for the telehealth consultation. The request type 1102 can be selected from a list of predefined categories displayed on the smart TV 102 when the app 114 is opened such as stroke, sepsis, hypoxia, heart failure, and other categories. In further examples, the request type 1102 can be selected from a list of predefined categories displayed on the mobile device 106.

In further examples, the patient P or the caregiver in the patient environment PE (e.g., the nurse N shown in FIG. 6), can speak one or more words to describe the request type, and the speaker and microphone unit 130 of the smart TV 102 recognizes the speech, and matches a request type based on the one or more spoken words to generate the telehealth consultation request 1100. In yet further examples, the mobile device 106 can recognize speech from the patient or the caregiver in the patient environment PE, and matches a request type based on one or more spoken words to generate the telehealth consultation request 1100.

In some examples, the description 1104 can be typed using the remote control 108 to select letter and number keys from a keyboard displayed on the smart TV 102 when the app 114 is opened. For example, the description 1104 can briefly explain a medical symptom such as "chest pain", "dizziness", "shortness of breath", "fever", and the like. In further examples, the description 1104 can be spoken by the patient P or the caregiver in the patient environment PE (e.g., the nurse N shown in FIG. 6), and the speaker and microphone unit 130 of the smart TV 102 recognizes the speech and converts the speech to text for drafting the description 1104 for incorporation into the telehealth consultation request 1100. In further examples, the description 1104 can be entered into the telehealth consultation request 1100 through typing or speech recognition on the mobile device 106 located in the patient environment PE.

Referring back to FIG. 10, the method 1000 includes an operation 1004 of acquiring relevant patient data based on one or both of the request type 1102 and the description 1104 included in the telehealth consultation request. In some examples, the relevant patient data acquired in operation 1004 is encrypted for enhanced data security.

The relevant patient data can include trends of physiological data values that are indexed based on one or more types of events such as prior consultations, lab results, health interventions such as surgeries, administered medications, and treatments, and health events such as heart attack, stroke, and the like. The relevant patient data can be indexed to include data values and trends for a predetermined period of time before the event and for a predetermined period of time after the event allowing for visualization of correlations between changes in the relevant patient data and possible causes due to the one or more types of events.

In operation 1004, the telehealth device 200 acquires the relevant patient data, such as notes from prior consultations, lab results, scans, administered medications, health interventions including surgeries and procedures performed on the patient, physiological parameters acquired from the monitoring device 122, and other information from the EMR 302 of the patient stored in the EMR system 300 via the communications network 124 (see FIG. 2). In some examples, the telehealth device 200 acquires the relevant patient data directly from the monitoring device 122 located in the patient environment PE via the communications network 124.

As an illustrative example, when the request type 1102 is a stroke consultation, operation 1004 can include acquiring patient data relevant to providing a diagnosis, a prognosis, or a treatment plan for stroke such as whether the patient has received blood thinners, what type of blood thinners were administered, last known computerized tomography (CT) scan, and other relevant information for a stroke consultation. Also, the patient data can include indexed physiological data values and trends before and after a stroke is detected or diagnosed.

As another illustrative example, when the description 1104 includes symptoms such as "chest pain", operation 1004 can include acquiring patient data relevant to the heart health of the patient such as heart rate, heart rate variability, blood pressure, respiration rate, and other relevant information for a cardiology consultation. Additional examples are contemplated.

Next, the method 1000 includes an operation 1006 of initiating the telehealth consultation. For example, the telehealth consultation can be initiated upon acceptance of the telehealth consultation request 1100 on the telehealth device 200 by the remote clinician.

Next, the method 1000 includes an operation 1008 of displaying on the display device 210 of the telehealth device 200 the relevant patient data acquired in operation 1004 together with a video stream of the patient environment PE captured by the camera 104. The video stream of the patient environment PE can be encrypted for enhanced data security.

In some examples, the relevant patient data is overlayed on the video stream of the patient environment PE. In other examples, the relevant patient data is displayed next to the video stream of the patient environment PE. In further examples, the video steam of the patient environment PE is displayed as a display widget that occupies a portion of a user interface displayed on the display device 210, and the relevant patient data is displayed in one or more additional display widgets that occupy additional portions of the user interface.

Figure 12:
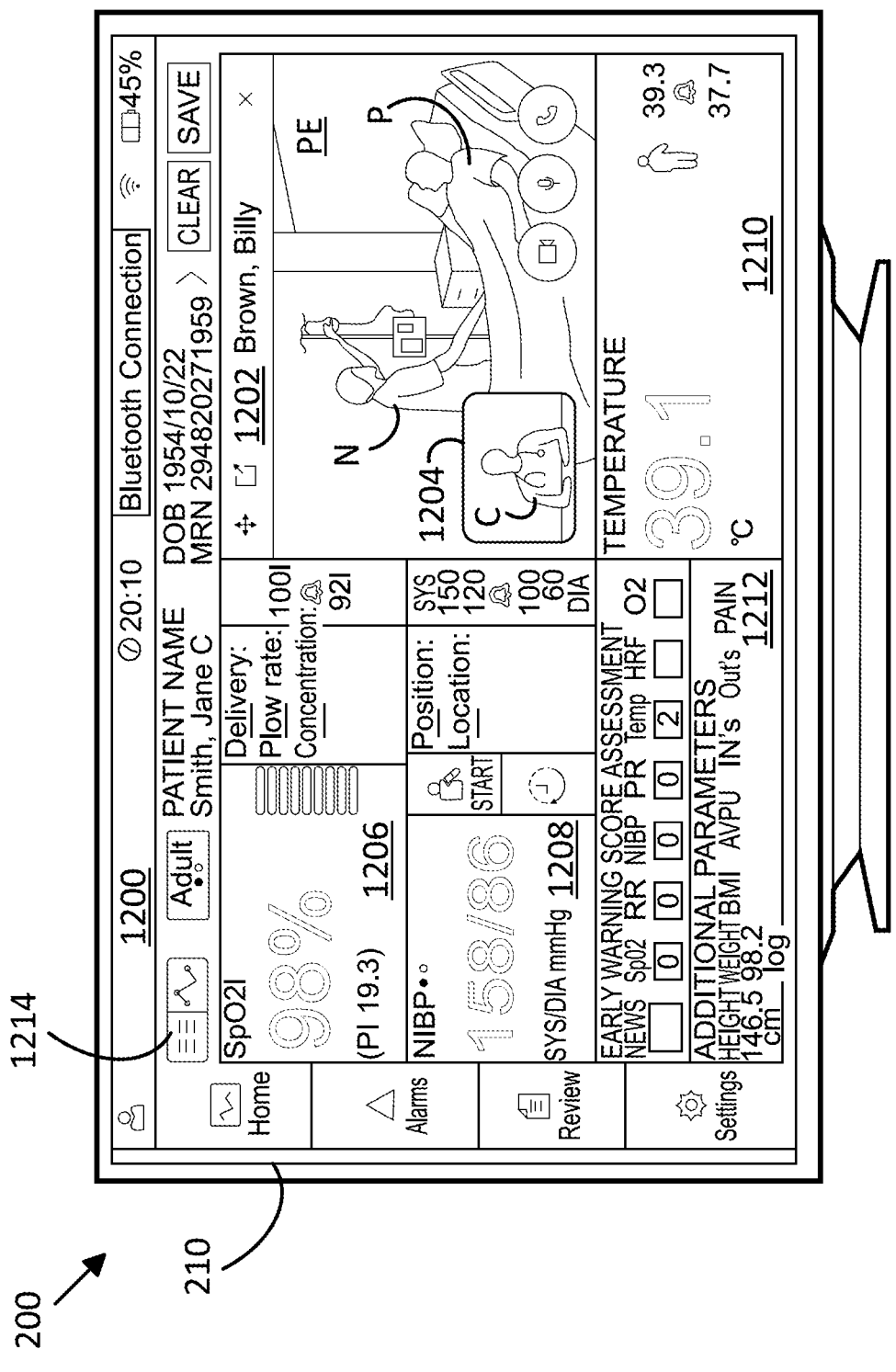
FIG. 12 shows another example of a user interface on the telehealth device of FIG. 1.

FIG. 12 shows an example of a user interface 1200 that can be displayed on the display device 210 of the telehealth device 200 in accordance with an example of operation 1008. In this example, the user interface 1200 includes a window 1202 displaying a video stream of the patient environment PE. In this example, the window 1202 includes a video stream of the patient P and nurse N captured by the camera 104 inside the patient environment PE. The user interface 1200 can further include a window 1204 for displaying a video stream of the remote clinician C that is captured by the camera 212 of the telehealth device 200.

The user interface 1200 additionally includes display widgets 1206-1212 that are optimized based on the telehealth consultation request 1100. For example, the display widgets 1206-1212 are custom selected and/or modified to display relevant patient data based on one or both of the request type 1102 and the description 1104 included in the telehealth consultation request. In such examples, the user interface 1200 can display only data elements relevant to the patient P's clinical condition. The display widgets 1206-1212 can display both current physiological data values and trends, as well as physiological data values and trends indexed for a predetermined period of time before and after an event (e.g., stroke) allowing for visualization of correlations between changes in the patient data and possible causes from the event.

In the example shown in FIG. 12, the user interface 1200 includes a display widget 1206 for displaying blood oxygen saturation (SpO2) of the patient P, a display widget 1208 for displaying non-invasive blood pressure (NIBP) including both systolic and diastolic blood pressure values of the patient P, a display widget 1210 for displaying temperature of the patient P, and a display widget 1212 for displaying additional parameters of the patient P such as height, weight, body mass index (BMI), Alert, Voice, Pain, Unresponsive (AVPU) score, early warning score assessment, and other patient data relevant to the telehealth consultation request 1100. Additional examples of display widgets that can be custom selected and/or modified to display relevant patient data based on the telehealth consultation request 1100 are possible. Also, the user interface 1200 can provide an icon 1214 selectable by the remote clinician C to manually view additional patient data and information not included in the display widgets 1206-1212.

Referring back to FIG. 10, the method 1000 can further include an operation 1010 of receiving a trigger event from the remote clinician C. The trigger event is received during the telehealth consultation such as when the patient P indicates a time for when an onset of a health condition or symptom started (e.g., chest pain). The trigger event can include the type of health condition or symptom (e.g., chest pain), and the date/time of its onset. The remote clinician C can manually enter the trigger event on the display device 210 of the telehealth device 200. Alternatively, the trigger event can be recognized by the speaker and microphone unit 214 of the telehealth device 200 (see FIG. 2) based on the conversation the remote clinician C has with the patient P and/or the caregiver (e.g., nurse N) during the telehealth consultation.

Next, the method 1000 includes an operation 1012 of automatically adjusting the display widgets 1206-1212 based on the trigger event received during the telehealth consultation. For example, the display widgets 1206-1212 can be custom selected, filtered, and/or modified to display relevant patient data based on the trigger event received in operation 1010. For example, the display widgets 1206-1212 can be customized to display patient data relevant to the health condition or symptom, and can filter the relevant patient data to display information aligned with the onset of the health condition or symptom (e.g., 30 minutes before and after onset).

The method 1000 when implemented on the telehealth device 200 eliminates the need for the remote clinician C to manually search and select relevant patient data alongside other irrelevant data from the EMR 302 of the patient P during a telehealth consultation. This can save time for the remote clinician C to view and interpret relevant patient data and thus lead to faster clinical decision making, which can reduce the time needed to provide urgent medical interventions, and thereby improve medical outcomes for critical health conditions.

The various embodiments described above are provided by way of illustration only and should not be construed to be limiting in any way. Various modifications can be made to the embodiments described above without departing from the true spirit and scope of the disclosure.

What is claimed is:

1. A system for providing telehealth consultations, the system comprising:
 a display device located in a patient environment;
 a camera operatively connected to the display device, the camera configured to capture a video stream of the patient environment; and
 a telehealth device remotely located with respect to the patient environment, the telehealth device including:
  at least one processing device; and
  a memory device storing instructions which, when executed by the at least one processing device, cause the telehealth device to:
   initiate a telehealth consultation on the display device;
   cause the camera to adjust the video stream of the patient environment during the telehealth consultation;
   determine relevant patient data based on the telehealth consultation;
   acquire the relevant patient data from at least one of a monitoring device located in the patient environment and an electronic medical record (EMR) system;
   display on a display of the telehealth device the relevant patient data and the video stream of the patient environment during the telehealth consultation, wherein the relevant patient data and the video stream of the patient environment are displayed within a user interface;
   detect an event during the telehealth consultation, the event indicating a health condition or a symptom; and
   filter the display of the relevant patient data based on the event to display physiological data from the at least one of the monitoring device and the EMR system relevant to the health condition or the symptom that triggered the event, wherein the physiological data is aligned with an onset of the health condition or the symptom that triggered the event by including physiological data values for a predetermined period of time before the event and for a predetermined period of time after the event, and wherein the user interface is automatically adjusted to display both current physiological data values and trends, as well as physiological data values and trends indexed for the predetermined period of time before the event and the predetermined period of time after the event allowing for visualization of correlations between changes in the relevant patient data and possible causes for the event.

2. The system of claim 1, wherein the instructions further cause the telehealth device to:
 pan the camera from side to side, tilt the camera up and down, and adjust an optical zoom of the camera based on inputs received during the telehealth consultation.

3. The system of claim 1, wherein the instructions further cause the telehealth device to:
 cause the camera to track movements of an object identified in the patient environment.

4. The system of claim 3, wherein the object is identified by facial recognition.

5. The system of claim 1, wherein the instructions further cause the telehealth device to:
 adjust playback of media content on the display device unrelated to the telehealth consultation.

6. The system of claim 1, wherein the telehealth device includes a camera for capturing a video stream of a remote clinician, and wherein the instructions further cause the telehealth device to:
 cause the display device to display the video stream of the remote clinician.

7. The system of claim 1, wherein the relevant patient data is selected for display based on a type of health condition or a symptom included in a request for the telehealth consultation.

8. A device for conducting a telehealth consultation, the device comprising:
 at least one processing device; and
 a memory device storing instructions which, when executed by the at least one processing device, cause the device to:
  receive a request for the telehealth consultation;
  determine relevant patient data based on a type of health condition or a symptom included in the request for the telehealth consultation;
  acquire the relevant patient data from at least one of a monitoring device located in a patient environment and an electronic medical record (EMR) system;
  display the relevant patient data and a video stream of the patient environment during the telehealth consultation, wherein the relevant patient data and the video stream of the patient environment are displayed within a user interface;
  detect an event during the telehealth consultation, the event indicating another type of health condition or symptom; and
  filter the display of the relevant patient data based on the event to display physiological data from the at least one of the monitoring device and the EMR system relevant to the another type of health condition or symptom that triggered the event, wherein the physiological data is aligned with an onset of the another type of health condition or symptom that triggered the event by including physiological data values for a predetermined period of time before the event and for a predetermined period of time after the event, and wherein the user interface is automatically adjusted to display both current physiological data values and trends, as well as physiological data values and trends indexed for the predetermined period of time before the event and the predetermined period of time after the event allowing for visualization of correlations between changes in the relevant patient data and possible causes for the event.

9. The device of claim 8, wherein the event is automatically detected from speech recognition during the telehealth consultation.

10. The device of claim 8, wherein the instructions further cause the telehealth device to:
 initiate the telehealth consultation on a display device located in the patient environment; and
 cause a camera operatively connected to the display device to adjust the video stream of the patient environment during the telehealth consultation.

11. The device of claim 10, wherein the instructions further cause the telehealth device to:

pan the camera from side to side, tilt the camera up and down, and adjust an optical zoom of the camera based on inputs received during the telehealth consultation.

12. A method of conducting a telehealth consultation, the method comprising:

receiving a request for the telehealth consultation;

determining relevant patient data based on a type of health condition or a symptom included in the request for the telehealth consultation;

acquiring the relevant patient data from at least one of a monitoring device located in a patient environment and an electronic medical record (EMR) system;

initiating the telehealth consultation on a display device in the patient environment;

causing a camera operatively connected to the display device to adjust a video stream of the patient environment during the telehealth consultation;

displaying the relevant patient data together with the video stream of the patient environment during the telehealth consultation, wherein the relevant patient data and the video stream of the patient environment are displayed within a user interface;

detecting an event during the telehealth consultation, the event indicating another type of health condition or a symptom; and filtering the display of the relevant patient data based on the event to display physiological data from the at least one of the monitoring device and the EMR system relevant to the another type of health condition or symptom that triggered the event, wherein the physiological data is aligned with an onset of the another type of health condition or symptom that triggered the event by including physiological data values for a predetermined period of time before the event and for a predetermined period of time after the event, and wherein the user interface is automatically adjusted to display both current physiological data values and trends, as well as physiological data values and trends indexed for the predetermined period of time before the event and the predetermined period of time after the event allowing for visualization of correlations between changes in the relevant patient data and possible causes for the event.

13. The method of claim 12, further comprising:
causing the camera to track movements of an object identified in the patient environment.

14. The method of claim 12, further comprising:
encrypting the relevant patient data and the video stream of the patient environment.

15. The method of claim 12, further comprising:
confirming an identity of a patient in the patient environment by using at least one of facial recognition, an admissions, transfer, discharge data feed, and bed or patient location determination by a real-time locating system.

* * * * *